US006407811B1

United States Patent
Snyder et al.

(10) Patent No.: US 6,407,811 B1
(45) Date of Patent: Jun. 18, 2002

(54) AMBIENT METHODS AND APPARATUS FOR RAPID LASER TRACE CONSTITUENT ANALYSIS

(75) Inventors: Stuart C. Snyder; Judy K. Partin; Jon D. Grandy, all of Idaho Falls; Charles L. Jeffery, Blackfoot, all of ID (US)

(73) Assignee: Bechtel BWXT Idano, LLC, Idaho Falls, ID (US)

( * ) Notice: Subject to any disclaimer, the term of this patent is extended or adjusted under 35 U.S.C. 154(b) by 0 days.

(21) Appl. No.: 09/440,786

(22) Filed: Nov. 15, 1999

(51) Int. Cl.$^7$ .................................................. G01J 3/30
(52) U.S. Cl. ...................................................... 356/316
(58) Field of Search ................................. 356/316–318

(56) References Cited

U.S. PATENT DOCUMENTS

| 5,206,716 A | 4/1993 | Beer et al. .................. 436/140 |
| 5,379,103 A | * 1/1995 | Zigler .......................... 356/73 |
| 5,847,825 A | * 12/1998 | Alexander .................. 356/318 |

OTHER PUBLICATIONS

Kim, D.E., "Quantitative Analysis of Aluminum Impurities in Zinc Alloy by Laser–Induced Breakdown Spectroscopy," *Applied Spectroscopy*, pp. 22–29 (Accepted for publication Jul. 16, 1996).

Kim, Y.W., "Molten Metal Analysis by Laser Produced Plasmas—Technical Progress Report", *Energy Conservation* for U.S. Department of Energy Office of Industrial Technologies, Washington, D.C., by Lehigh University (Bethlehem, PA), pp. 1–42 (Jul. 1994).

Paksy, L., et al., "Production control of metal alloys by laser spectroscopy of the molten metals. Part I. Preliminary Investigations," *Spectrochimica Acta Part B*:51, pp. 279–290 (1996).

Quentmeier, A., et al., "Internal standardization in laser induced fluorescence spectrometry of microplasmas produced by laser ablation of solid smaples," *Spectrochimia Acta*, vol. 45B No. 6, pp. 537–546 (1990).

Savage, N., "Laser aims to analyze rocks on Mars," *Laser Focus World*, pp. 54–55 (May 1999).

Snyder, S.C., et al., "An Investigation of Laser–induced Breakdown Spectroscopy Augmented by Laser–induced Fluorescence," presented at Laser Instutite of America Proceedings, vol. 85c, Laser Materials Processing Process Diagnostics And Control, pp. 254–261 (Nov. 16–19, 1998).

Sdorra, W., et al., "Basic Investigations for Laser Microanalysis: II. Laser–Induced Fluorescence in Laser–Produced Sample Plumes," *Mikrochim. Acts [Wien] II*, pp. 201–218 1989.

* cited by examiner

*Primary Examiner*—Frank G. Font
*Assistant Examiner*—Michael P. Stefila
(74) *Attorney, Agent, or Firm*—Dahl & Osterloth

(57) ABSTRACT

A method and apparatus are disclosed for measuring trace amounts of constituents in samples by using laser induced breakdown spectroscopy and laser induced fluorescence under ambient conditions. The laser induced fluorescence is performed at a selected wavelength corresponding to an absorption state of a selected trace constituent. The intensity value of the emission decay signal which is generated by the trace constituent is compared to calibrated emission intensity decay values to determine the amount of trace constituent present.

37 Claims, 3 Drawing Sheets

US 6,407,811 B1

AMBIENT METHODS AND APPARATUS FOR RAPID LASER TRACE CONSTITUENT ANALYSIS

CONTRACTUAL ORIGIN OF THE INVENTION

The United States Government has rights in this invention pursuant to Contract No. DE-AC07-94ID13223 between the United States Department of Energy and Lockheed Martin Idaho Technologies Company, now Contract No. DE-AC07-99ID13727 with Bechtel BWXT Idaho, LLC.

FIELD OF THE INVENTION

This invention relates to a laser spectroscopy method and apparatus for detecting and measuring the presence of individual constituent elements or molecules in a sample, particularly trace amounts of such constituents. More particularly, the invention relates to laser ablating a solid sample and creating a plasma from the ablated material. The ablated plasma is then subjected to another laser beam to excite-fluoresce an absorption state of a particular constituent. The relative amount of the particular constituent is determined by measuring the decay emission values of the excited absorption state and comparing it to decay emission values of samples of known trace constituent composition. The method is rapid and may be carried out in the atmosphere and under actual industrial situations. The apparatus is adaptable for field operation.

BACKGROUND OF THE INVENTION

There are many situations where it is necessary or desirable to obtain substantially instantaneous trace constituent analysis of a sample material. For example, real time analysis of trace constituent contamination in the manufacture of copper cathodes enables continuous process control to ensure their elimination. Similar advantages can be obtained in the electrolytic manufacture of aluminum and its alloys. Such analysis also facilitates the purification and alloying of molten metals such as steel, cast iron, aluminum, brass, nickel alloys and such. Ideally such trace constituent analysis can be done without complex and time consuming sample preparation. Rapid trace constituent analysis is also desirable for detecting minute levels of heavy metals, dangerous substances or other contaminants in water, air or soil. Detecting impurities in thermal waste processes is also desirable for pollution control. To be practical, any such analysis should be done in the air or in the existing ambient atmosphere.

Recently, laser-induced breakdown spectroscopy (LIBS) has been used as a tool for real-time, in situ, primary composition and impurity analysis. In LIBS, a pulsed laser beam is focused onto a sample. This produces intense radiation that vaporizes, or ablates, a minute portion of the sample and forms a high temperature plasma from the ablated material. The excited atoms and ions in the plasma emit light that has a frequency characteristic of the emission states of the elements and molecules present in the sample. The composition of a sample is determined by analysis of the emission spectrum of the plasma as the atoms return to lower and ground states after laser radiation.

An advantage of the LIBS process is that a very small amount of material is ablated by the laser, typically only about 1 to 25 $\mu$g for solid samples. Accordingly, for most applications, LIBS compositional analysis is considered nondestructive testing.

Another advantage of LIBS is that it is relatively easy to set up and is field deployable using modem portable pulsed lasers, fiber optic sensors, commercial photodetectors, emission spectrum analyzers, and such.

A serious disadvantage of LIBS is that it is inaccurate for determining the presence of trace amounts of elemental constituents, particularly those present in quantities less than about 100 parts per million (ppm). The generally weak spectral signals emitted by trace element constituents are difficult or impossible to separate from the background noise of a typical, complex, LIBS spectrum. Accordingly, the LIBS process has not been acceptable for doing real-time trace element analyses.

Experimental physicists have improved the detection limits of LIBS by probing the plasma created by LIBS with a second laser beam having a predetermined energy. The second beam is tuned to excite a fluorescent transition or absorption state of an ablated element or molecule of interest in the plasma. This process of laser induced fluorescence (LIF) has produced experimentally verifiable detection limits of about 10 ppm or greater for steel, for example. A drawback of this process has been that it must be practiced in a low pressure buffer gas (such as argon) or a vacuum to optimize emission yields. Creating and handling LIBS produced samples in a controlled, evacuated environment is time consuming, costly, and greatly inhibits the practical use of LIF in the field, foundry or factory.

Accordingly, there has been a long felt need for a method and apparatus for rapidly detecting trace amounts of elemental or molecular constituents in samples under practical conditions. In particular, there has been a need to detect the presence of trace constituents in the parts per billion range using a practical, field operative system.

SUMMARY OF THE INVENTION

In accordance with a preferred embodiment of the invention, a method and apparatus are provided for rapidly analyzing trace amounts of constituents in samples under ambient conditions. The invention has particular application to the identification of trace elements in copper cathode materials. By trace amounts herein, we generally mean amounts in the hundreds of parts per million or less.

The method comprises exposing a sample to a first laser beam which is of suitable wavelength and intensity to ablate a micro-specimen from the surface of a solid, or to completely vaporize a liquid and/or gaseous sample. The energy of the laser beam causes a plasma of the micro-specimen to form, which plasma has substantially the same composition as the sample.

Before this plasma decays, it is exposed to a second laser beam which is tuned to is have a wavelength and energy corresponding to an absorption state of a trace constituent of interest. This second laser radiation excite-fluoresces the selected absorption state and intensifies its decay emission.

The intensity value of the decay of the fluoresced element is measured and compared to a calibrated emission spectrum decay value.

In a preferred method in accordance with the invention, a sample is suitably located with respect to the analysis apparatus. A laser, such as a pulsed Nd:YAG laser, is focused on the sample and pulsed to ablate a micro-sample and form a micro-plasma. A tunable laser such as a dye laser or pumped optical parametric oscillator is used to pulse the plasma before it degrades substantially, thereby fluorescing an absorption state of a constituent of interest in the sample and increasing the emission spectrum.

In a preferred embodiment, means are provided to sequence the pulsing of the first and tuned lasers. A fiber optic is used to detect the emission radiation of the fluoresced plasma. The radiation output is fed to a monochromator or other spectrum analyzer the output of which is processed by a detector. The output of the detector is analyzed by a conventional computer processor and the background noise is subtracted. The net emission spectrum is compared to precalibrated spectrum concentration values for the constituent. Such calibrated concentration values are obtained by performing the subject method on samples having known amounts of the constituent being examined.

A preferred apparatus for this invention comprises a high energy pulsed laser for ablating a few micrograms of a sample and forming a plasma therefrom. A tunable laser is provided to excite-fluoresce a transition of a desired element or molecule of interest in the plasma. The high energy pulsed laser and tunable laser are sequenced by a delay generator.

The emission spectrum of an excite-fluoresced transition is sensed by a probe and fed to a monochromator. The output of the monochromator is analyzed by a sensor array. A portable computer is used to assemble the data and calculate the actual concentration of the constituent in the sample.

DETAILED DESCRIPTION OF THE INVENTION

Figure 1:
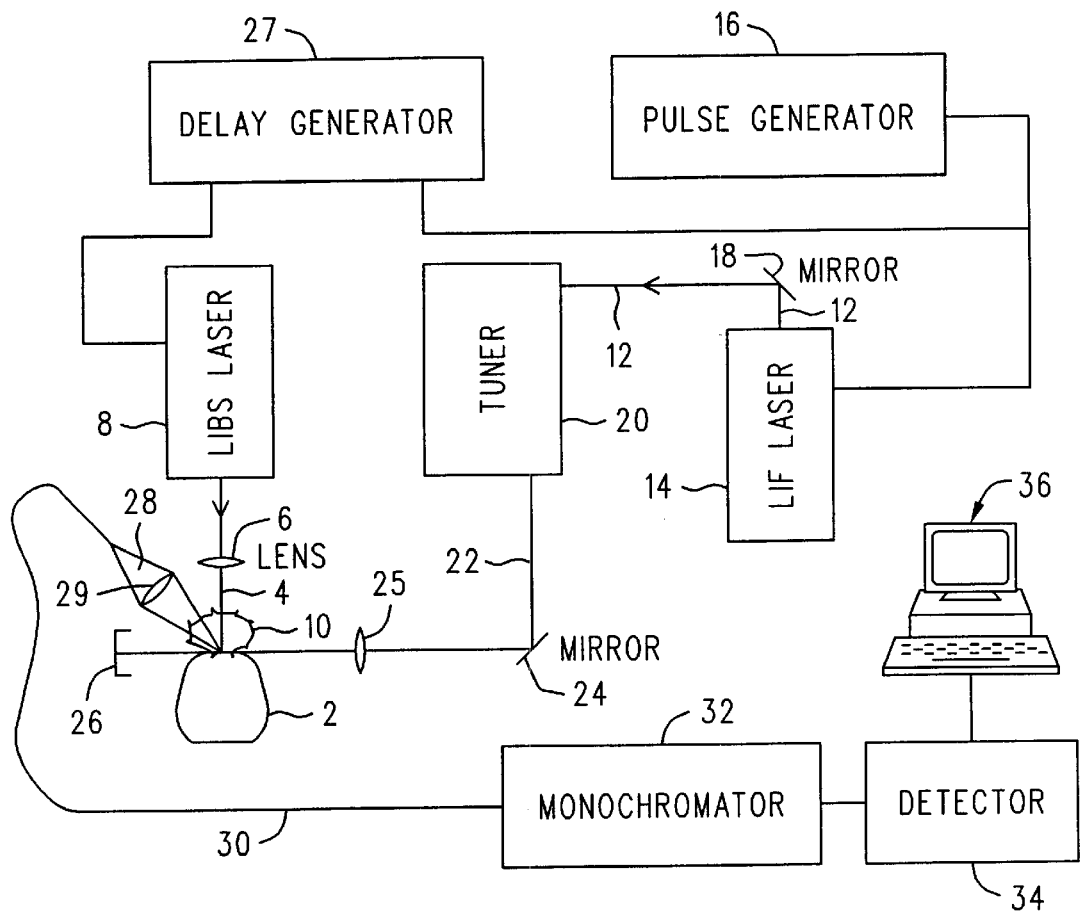
FIG. 1 is a schematic view of an apparatus for using laser induced breakdown spectroscopy and laser induced fluorescence to determine the amount of a constituent present in a sample.

According to the invention, a method and apparatus are provided for rapidly analyzing the presence of a constituent in a sample. The apparatus is used, and the method carried out, under ambient conditions. That is, the invention may be practiced regardless of the composition of the surrounding atmosphere or the physical environment. Generally, the ambient atmosphere is air at atmospheric pressure. However, the invention may also be practiced in other atmospheres such as those encountered in chemical or electro-chemical manufacturing plants, in semiconductor manufacture, and in foundries. Creation of a vacuum or inert atmosphere is unnecessary for the practice of the invention.

In a preferred embodiment, and with respect to solid samples, a first laser beam having a suitable wavelength and intensity is focused onto the sample. Exposure to the laser beam causes a micro-sample or micro-specimen to ablate from its surface. By ablating or ablation herein we mean the process of removing a micro-specimen from the surface of a sample by exposing it to a laser beam. In the practice of this invention, a sample in the weight range of from about 0.5 to 25 micrograms is ablated. For most situations, therefore, the amount of material removed from a sample is so small that our method is considered to be non-destructive. While no special preparation of solid samples is usually required, if the sample surface is dirty, tarnished, or for some other reason has a composition different that the bulk of the sample, it should be cleaned by any well known method before ablating. The method is particularly effective for determining the presence of trace elements in metals such as copper, iron, nickel, titanium, and aluminum The wavelength and intensity of the first laser beam are calibrated and controlled to provide sufficient energy to ablate the elements and molecules of a sample and to assure that the composition of the ablated micro-specimen is substantially the same as the composition of the bulk sample material. In accordance with the invention and particularly for measuring trace elements in metal samples, a LIBS laser power density of at least about 15 GW/cm$^2$ is desired.

A laser beam-solid sample surface interaction depends on the absorptivity of the solid at a given laser wavelength, the structure of the solid, the laser pulse width and pulse rate, and the intensity of the laser light focused on the sample. Increased mass ablation rates for laser induced breakdown spectroscopy are favored by shorter laser wavelengths. Ablation rates are also less dependent on the surface type and topography of a sample if high-intensity pulses are used. High intensity pulses also tend to reduce selective ablation, however the laser beam-solid surface interaction is not fully understood by the scientific community at this time.

It is not necessary to ablate fluid samples, i.e. liquid and gaseous samples, before practicing the subject method. However, fluid samples are also subjected to the first laser pulse to vaporize them. Exposure of both liquid and gaseous samples to the first laser beam also forms a plasma having the composition of the sample.

Substantially simultaneously with the delivery of the first laser pulse, the elements and molecules of ablated solid, liquid, or gas are excited into forming a plasma. Herein this plasma may be referred to as a "micro-plasma" because such small amounts of material form them. By plasma herein we mean a highly ionized gas having equal numbers of ions and electrons in the excited state after exposure to a laser beam and before the excited electrons drop to lower energy states, the elements return to their ground states, and the plasma decays. This technique of forming a plasma and the subsequent analysis of the plasma breakdown spectrum is often referred to in the literature as laser induced breakdown spectroscopy or LIBS.

While our invention is not to be limited by the physics of laser induced breakdown spectroscopy, it is believed that the following occurs. In the case of solids, the intense laser pulse is initially absorbed causing vaporization of sample material (ablation) and the creation of a shock wave. Within a few nanoseconds of the pulse, the laser beam generates free electrons by multiphoton ionization, the rate of generation of which is dependent on the laser wavelength. The free electrons themselves absorb laser radiation by an inverse bremsstrahlung absorption mechanism and generate more free electrons by collisions with atoms in the vapor. This in turn leads to more absorption of radiation by inverse bremsstrahlung absorption and a condition known as thermal runaway occurs for the duration of the laser pulse. During laser beam exposure, temperatures in the plasma are generally on the order of $10^4$ to $10^{5°}$ K. and the plasma itself has an extremely high energy density.

Thermal runaway sustains the luminosity or continuum emission, i.e., emission across most of the visible light spectrum, of the plasma for a time as long as 10 microseconds after the laser pulse ends. This continuum spectrum is so dense that it cannot be practically used to make compositional determinations of a micro-sample. However, as the micro-plasma cools and the free electrons recombine with ions, emission lines from individual constituents are produced in the "afterglow" spectrum. Shortly after electron absorption commences, emission lines produced when neutral constituents return to the ground state appear. The phenomena persists for up to about 100 microseconds until the plasma decays completely.

The intensity of a spectral emission line radiated from a LIBS micro-plasma is proportional to the number density of the constituents in the excited state multiplied by s the transition probability. If the number density is low, as in the case of trace constituents, or the transmission probability is weak, the emission lines are buried in the background radiation spectrum and the various trace constituents are undetectable by laser induced breakdown spectroscopy alone.

As discussed above, laser induced fluorescence spectroscopy is used in conjunction with laser induced breakdown spectroscopy to greatly increase the detectability of trace constituents in a sample. A second pulsed laser beam is tuned to a wavelength corresponding to an absorption state of a constituent element of interest. The beam is focused on the laser induced breakdown micro-plasma during afterglow. Ideally, the second laser excitation occurs before the plasma is extinguished but while atoms or molecules are mostly in the ground state. This delay is typically several microseconds for a micro-plasma created by a 10 to 50 nanosecond laser pulse. Exposure of the microplasma to the second laser beam excite fluoresces the selected absorption state of the selected element and greatly intensifies its decay emission. For trace element analysis of metals, the power density of the second pulsed laser beam is from about 300 MW/cm$^2$ to 500 MW/cm$^2$.

Prior art LIBS/LIF spectroscopy was practically limited to laboratory use because it required a vacuum or low pressure controlled environment for the sample during laser beam radiation. In this method, the micro-sample is surrounded by ambient gas to improve the formation of the micro-plasma. The ambient or surrounding gas may be air or another gas or gases present in the environment where the LIBS/LIF analysis is performed. For example, for certain chemical processes where LIBS/LIF is used to test for trace constituents of the product, the ambient gas could be nitrogen, an inert gas, a chemically active gas, not air. In typical ambient industrial or field environments, the vaporization of the sample by LIBS is more complete than in prior art processes. Furthermore, the plasma is denser and has a much more uniform composition.

Because the LIBS/LIF fluorescence emission is pulsed, gated detection techniques can be used to isolate the signal from the continuous background radiation and improve the signal to noise ratio. Background radiation noise may also be subtracted by exposing a micro-plasma to a tuned laser pulse at a slightly shorter wavelength than the laser induced fluorescence wavelength and subtracting out that emission spectrum from the laser induced fluorescence spectrum taken at the optimum wavelength. The intensity value of a laser induced fluorescent emission line, corrected as necessary, may be referred to herein as the "constituent emission intensity value" of an element or molecule in a micro-sample. This constituent emission intensity value is compared to the constituent emission intensity values for standard samples to determine the relative amount of an element present in an experimental sample. Any of the many methods of subtracting noise or background from radiation emission spectra, such methods being well known to those skilled in the art, may be used in the practice of this invention.

The actual amount of a constituent in a sample is obtained by comparing the measured constituent emission intensity value to a calibrated constituent emission intensity value. The calibrated values are obtained by exposing a number of standard samples of known composition to laser induced breakdown spectroscopy and laser induced fluorescence to obtain constituent emission intensity values for the selected emission lines under the conditions of the method of this invention.

FIG. 1 is a schematic representation of an apparatus for practicing the subject invention. FIG. 1 shows a sample 2 in the form of a solid metal ingot. A first laser beam 4 is focused through lens 6 onto sample 2. First laser beam 4 is generated by a first LIBS laser 8. While we used a Nd:YAG laser, any other laser with suitable wavelength and beam intensity may be used. First laser 8 is chosen based on such criteria as wavelength capabilities, intensity, cost, size, etc. As described above, first laser 8 generates a pulsed first laser beam 4 to ablate sample 2 and create a laser induced breakdown micro-plasma 10.

With further reference to FIG. 1, means are provided to provide a second, pulsed laser beam 12. Second laser beam 12 is generated by a second or LIF laser 14. LIF laser 14 is pulsed by pulse generator 16. Second laser beam 12 is directed by mirror 18 into wavelength tuner 20. Wavelength tuner 20 changes the wavelength of second laser beam 12 to match the wavelength of a selected fluoresced absorption state of a constituent in micro-plasma 10.

Wavelength tuner 20 may be a conventional tunable dye laser or an optical parametric oscillator (OPO) pumped by LIF laser 14. In a tunable dye laser, an organic dye solution circulates through the laser cavity where it is excited by an external laser such as a pulsed Nd:YAG laser. The fluorescence spectrum of the dye is broadband, however, a very narrow wavelength can be selected from the broadband of wavelengths by proper configuration of the laser cavity. The narrow wavelength light thus produced is amplified and lases. As the laser cavity configuration is changed, usually by adjusting a diffraction grating (not shown) that is the rear mirror of the cavity, the lasing wavelength changes.

In a tunable OPO laser, a crystal in the laser cavity is pumped by an external laser such as a pulsed Nd:YAG laser. The crystal converts the pumped laser light into signal and idler waves having different frequencies. The OPO laser wavelength is tuned by changing the orientation of the crystal.

Both tunable dye lasers and OPO lasers are well known to those skilled in the art and are selected based on such features as efficiency, wavelength range, cost, size, etc. Because the OPO laser is solid state, it is generally preferred for use in field applications. In principle, one could use a single laser for both LIBS and LIF employing an optical delay line. However, at this time we found it more practical to use two lasers.

Laser induced fluorescence beam 22 exits wavelength tuner 20, is focused by mirror 24 and passes through lens 25 to fluoresce micro-plasma 10. LIF beam 22 is generally delivered to micro-plasma 10 in a direction substantially normal to the direction of first laser beam 4. This is to promote optimal energy absorption of micro-plasma 10 by beam 22. Delay generator 27 sequences the pulsing of first LIBS laser 8 and LIF laser 14 to optimize the fluorescence, and subsequent emission decay, of micro-plasma 10. LIF beam 22 is absorbed by a beam stop 26, as necessary. The optical emission decay signal from the decay of the laser induced fluorescence of micro-plasma 10 is detected by sensor 28, focused through lens 29, and delivered through fiber optic cable 30 to a monochromator 32 which prepares the signal for detection by coherent light detector 34. Computer readable output from detector 34 is processed by computer 36, ultimately resulting in the determination of the amount of a particular constituent in sample 2.

Figure 2:
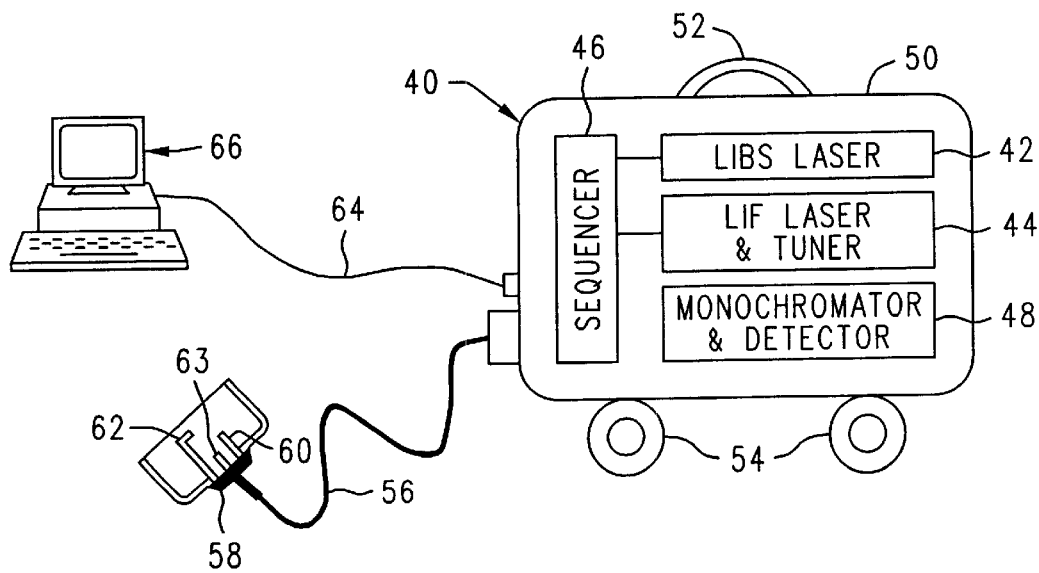
FIG. 2 is a conceptual representation of a portable apparatus in accordance with this invention.

FIG. 2 is a conceptual representation of a portable apparatus 40 for practicing the method of this invention. It features LIBS laser 42, LIF laser & tuner 44, sequencer 46, monochromator and detector 48, all internally located in portable cabinet 50 having 10 handle 52 and wheels 54. Conduit 56 extends from cabinet 50 and terminates in probe cover 58. Conduit 56 carries pulsed beams from LIBS laser 42 and LIF laser 44 through wave guides (not shown) to LIBS probe lead 60 and LIF probe 62. A fiber optic cable 63 carries the LIF emission decay signal to monochromator and detector 48. Detector output in computer readable form is directed through data cable 64 to be analyzed by portable computer 66. Recent advances in the energy efficiency and reduced sizes of the components described above facilitate the design and portability of the apparatus of the invention and its practical use in the field.

EXAMPLE

The unknown concentrations of trace amounts of the elements bismuth and lead were determined in a copper cathode. A neodymium-doped yttrium aluminum garnet (Nd:YAG) laser operating at 532 nm was used to generate the micro-plasma from copper samples with traces of other elements. A second Nd:YAG laser operating at 532 nm pumped a tunable dye laser to generate the LIF signal. Both lasers were externally triggered by a master oscillator with the dye laser trigger delayed relative to the initiation of the microplasma by an adjustable amount. The pulsed width of both of the lasers was about 10 nanoseconds and the pulse rate was 10 Hz. In order to excite fluoresce the selected trace elements, it was necessary to frequency double the dye laser fundamental wavelength using a potassium dihydrogen phosphate (KDP) crystal. Rhodamine 590 and sulforhodamine 640 laser dyes were used to generate the findamental wavelengths to excite the selected absorption states. The frequency-doubled laser-pulse energy was about 1 megaJoule per pulse. The LIBS generated micro-plasmas were all generated in air at room temperature.

A 500 mm focal length lens was used to focus 40 megaJoules of 532 nm laser light onto a solid copper sample to generate a micro-plasma. The laser induced fluorescence laser beam was focused into the micro-plasma with a 400 mm lens to a waist that was offset about 0.5 mm from the surface of the sample. The time delay between pulses was about 10 microseconds. Pulses were synchronized using a master oscillator and time delay circuit.

The LIF signal was collected with a 50.4 mm diameter 150 mm focal length lens and focused onto the end of a 200 pm core diameter fused silica optical fiber and transmitted to a 1 m focal length monochromator with an 1800 groove per mm diffraction grating for dispersion. The signal was then detected using a Princeton Instruments Model ICCD-576G/RB thermoelectrically-cooled, gated, two-dimensional, intensified charge-coupled device (ICCD) diode array. The ICCD array was gated on for about 50 nanoseconds at a time coincident to the laser induced fluorescent pulse.

Instead of measuring the peak intensity of the laser induced fluorescence signal for a constituent, an area about 0.35 nm wide, centered under the laser induced fluorescence spectral peak was integrated for 50 laser shots to increase the signal to noise ratio. By detuning the probe laser wavelength from the fluorescence resonance, the plasma background signal and dark current noise were measured and then subtracted out by the computer from the on-resonance signal to determine an intensity value for the constituent. The experimental set-up was similar to that shown in FIG. 1.

The copper samples used for calibration were purchased from the United States National Institute of Standards and Technology (NIST). The compositions of the samples were certified by NIST. Six 99.9% pure copper specimens containing from 0.5 ppm to 128 ppm lead and six other 99.9% pure copper specimens 0.2 to 24.5 ppm lead were tested.

The samples taken from the copper cathode and the NIST calibration samples were set in an epoxy block and polished to reveal flat, coplanar, copper surfaces. The flat epoxy block was then mounted on a motorized translation stage in order to slowly traverse the copper in the direction perpendicular to the 532 nm laser beam creating the micro-plasma. This was done so that the micro-plasma was continually generated over fresh copper. Care was taken to ensure that this translation was only perpendicular to the LIBS laser beam to maintain constant intensity of the beam to micro-plasmas.

Figure 3:
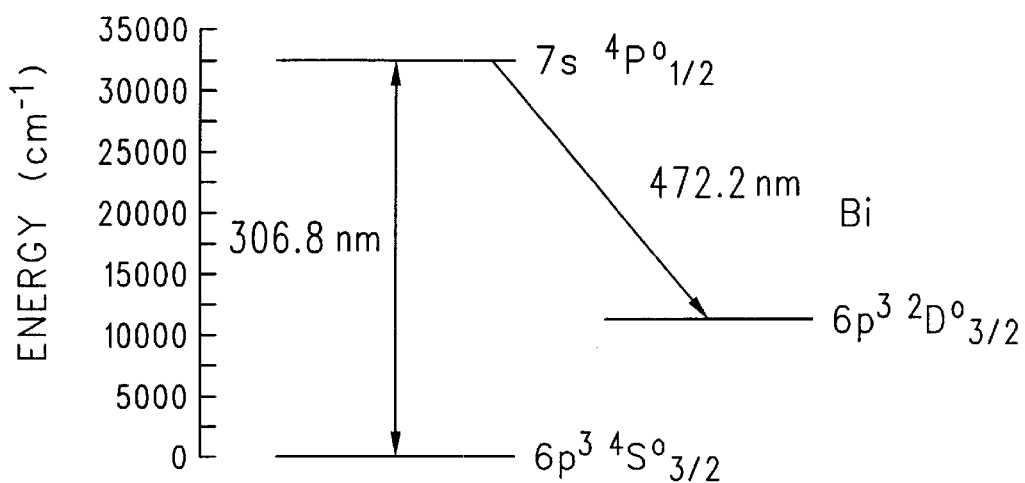
FIG. 3 is a partial energy level diagram of the atomic element bismuth showing an excitation level at 306.8 nanometers (nm) and fluorescent decay at 472.2 nm.
Figure 4:
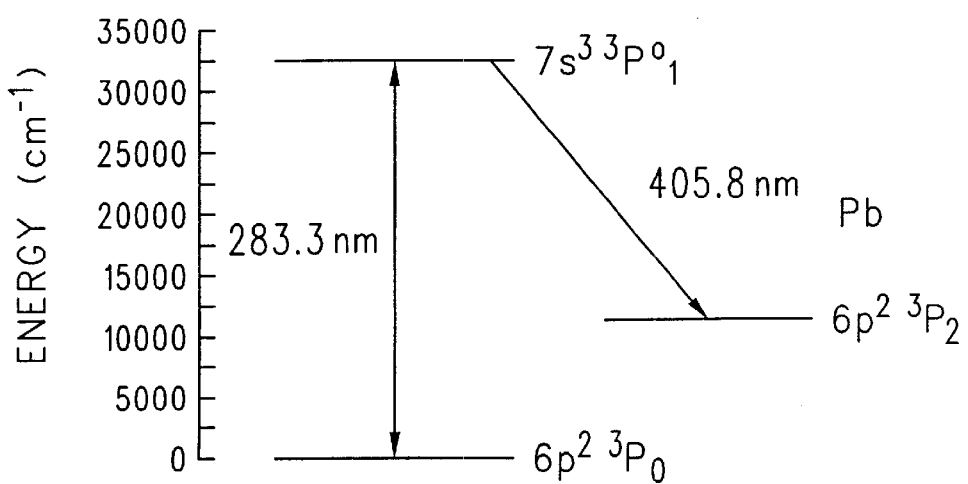
FIG. 4 is a partial energy level diagram of the atomic element lead showing an excitation level at 283.3 nm and fluorescent decay at 405.8 nm.

Referring to FIGS. 3 and 4, the LIF laser was tuned to the 306.8 nm energy state for detecting Bi and the 283.3 nm energy state for detecting lead. The laser induced fluorescent energy state observed for Bi was the $7\ s\ ^4p_{1/2}$ to $6p^3\ _2d^0_{3/2}$ 472.2 nm wavelength emission decay state. The laser induced fluorescent energy state observed for Pb was the $7\ s\ ^3p^0_1$ to $6p^2\ ^3p_2$ 405.8 nm wavelength emission decay state. These transitions were selected because they were of suitable wavelength for the available laser and relatively strong decay emissions compared to other excitation states.

Data were collected by means of a computer-controlled ICCD array operated in the photon counting mode. Photons emitted into a narrow spectral window during the fluorescent decay of the excited Bi or Pb impurity elements were counted. Photons were counted for 50 nanoseconds while the LIFS laser was fired. Limiting the spectrum of the detected light and the time of data acquisition helped reduce background noise and increased the signal to noise ratio. The NIST copper samples were first subjected to the LIBS/LIF process to generate calibration curves. Then the unknown concentrations of Bi is and Pb in the copper cathode were determined by subjecting samples from the cathode to the same process and comparing the output to the calibration curves.

Figure 5:
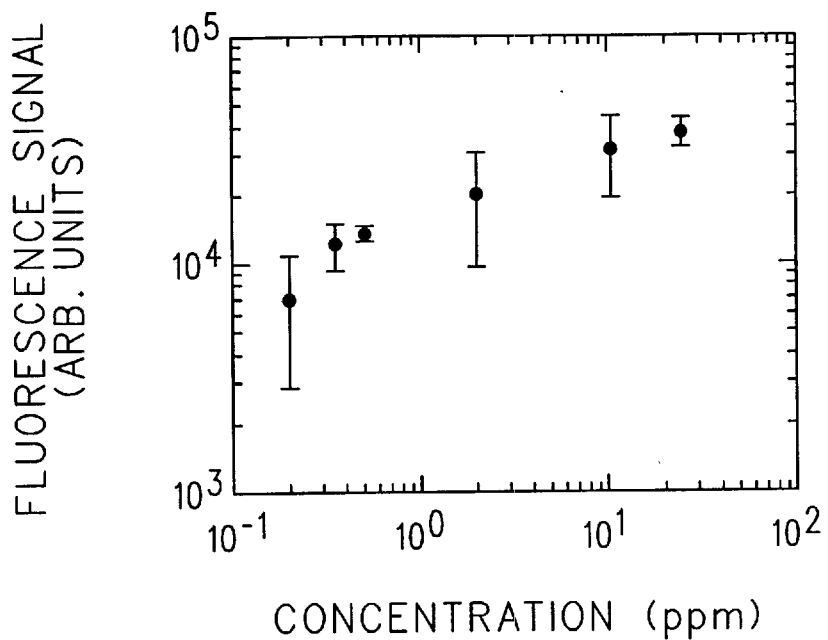
FIG. 5 is a plot of the signal intensity of the laser induced fluorescent 472.2 nm decay state signal of bismuth as a function of the concentration of bismuth in copper samples.
Figure 6:
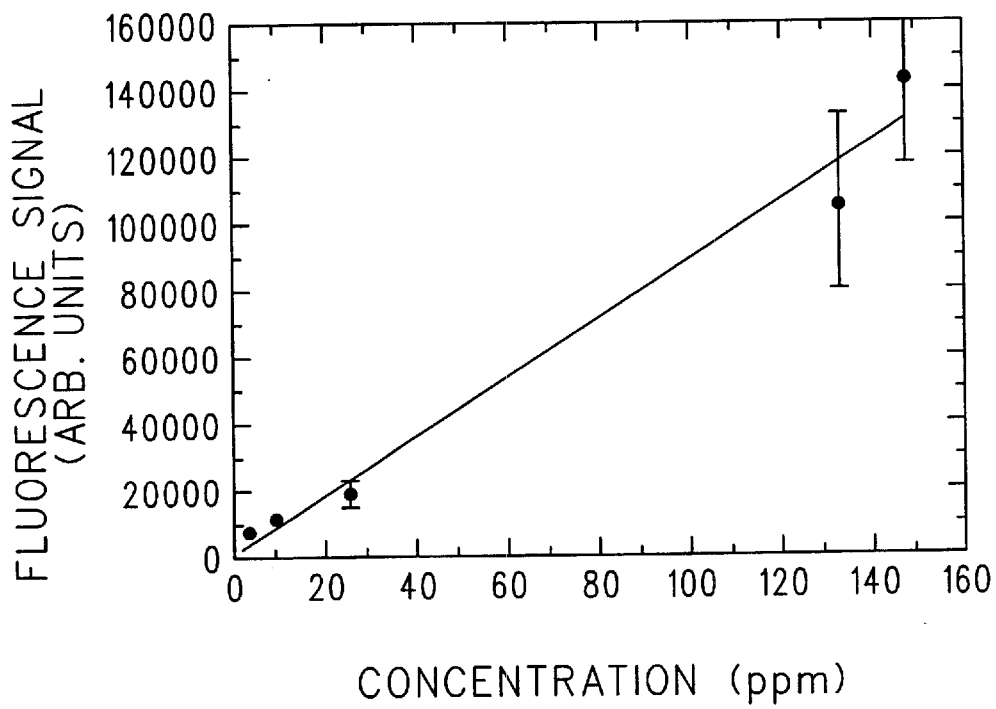
FIG. 6 is a plot of the signal intensity of the laser induced fluorescent 405.8 nm decay state signal of lead as a function of the concentration of lead in copper samples.

Plots of the laser induced fluorescence signal in arbitrary units, as a function of concentration of the concentrations of Bi and Pb in the NIST copper samples, are shown in FIGS. 5 and 6, respectively.

The LIF signals for all concentration levels were significant even at 200 parts per billion (ppb) Bi and 500 ppb Pb. Improvements to the laser power would increase experimental detection limit by at least an order of magnitude and reduce the uncertainty of the emission intensity values in the parts per billion trace element range.

While our invention has been described in terms of specific embodiments thereof, it is understood that other modes could be practiced by one skilled in the art. Accordingly, the scope of the invention is to be limited only in accordance with the following claims.

We claim:

1. An ambient method for rapidly analyzing the amount of a constituent present in a sample, the method comprising:

exposing a sample to a first laser beam, the beam having a wavelength and intensity suitable to ablate a micro-specimen from the sample surface and to form a plasma of the micro-specimen, the plasma having a composition substantially the same as the composition of the sample;

exposing the plasma to a second laser beam, the second laser beam having a wavelength corresponding to an absorption state of a constituent of the sample to thereby excite fluoresce the absorption state and intensify the decay emission of the state;

obtaining a constituent emission intensity value by measuring the intensity of the decay emission of the constituent absorption state; and comparing the constituent intensity value to a calibrated emission spectrum intensity value for the constituent.

2. The method of claim 1 wherein the sample is a metal.

3. The method of claim 1 wherein the power density of the first laser beam is at least about 15 GW/cm$^2$ and the power density of the second laser beam is about 300 MW/cm$^2$ to 500 MW/cm$^2$.

4. The method of claim 3 wherein the method is conducted in an air atmosphere.

5. The method of claim 1 wherein the second laser beam is tuned after generation to change its wavelength.

6. The method of claim 3 wherein the second laser beam is tuned by a dye laser to the wavelength corresponding to the absorption state of the constituent.

7. The method of claim 3 wherein the second laser beam is tuned by an optical parametric oscillator laser to the wavelength corresponding to the absorption state of the constituent.

8. The method of claim 1 wherein the first and second laser beams are generated by a Nd:YAG laser.

9. The method of claim 1 wherein the decay emission of the constituent absorption state is measured by an intensified charge-coupled device array.

10. The method of claim 1 wherein the second laser beam is oriented substantially normal to the first laser beam.

11. The method of claim 1 wherein the method is conducted in an air atmosphere.

12. An ambient method for rapidly analyzing the amount of a constituent present in a sample wherein the sample is a fluid, the method comprising:

exposing a sample to a first laser beam, the beam having a suitable wavelength and intensity to form a plasma of the micro-specimen, the plasma having a composition substantially the same as the composition of the sample;

exposing the plasma to a second laser beam, the second laser beam having a wavelength corresponding to an absorption state of a constituent to thereby excite fluoresce the absorption state and intensify the decay emission of the state;

obtaining a constituent intensity value by measuring the intensity of the decay emission of the constituent absorption state; and comparing the constituent intensity value to a calibrated emission spectrum intensity value for the constituent.

13. An ambient method for rapidly analyzing a trace constituent in a sample, the method comprising:

exposing a sample to a first laser beam having a suitable wavelength and intensity to ablate a micro-specimen from the sample surface and to form a plasma of the micro-specimen, the plasma having a composition substantially the same as the sample composition;

exposing the plasma to a second laser beam, the second laser beam having a wavelength corresponding to an absorption state of a trace constituent to thereby excite fluoresce the absorption state and intensify the decay emission of the absorption state;

exposing the plasma to a third laser beam, the third laser beam having a wavelength longer than the wavelength of the second laser beam;

obtaining a net constituent intensity value by measuring the intensity of the decay emission of the absorption state from the plasma exposed to the second laser beam and subtracting the intensity of the decay emission of the absorption state from the plasma exposed to the third laser beam; and comparing the net constituent intensity value to a calibrated emission spectrum intensity value for the constituent.

14. The method of claim 13 wherein the sample is a metal.

15. The method of claim 13 wherein the power density of the first laser beam is at least about 15 GW/cm$^2$ and the power density of the second laser beam is about 300 MW/cm$^2$ to 500 MW/cm$^2$.

16. The method of claim 13 wherein the method is conducted in an air atmosphere.

17. The method of claim 13 wherein the second laser beam is tuned after generation to change its wavelength.

18. The method of claim 13 wherein the second the laser beam is tuned by a dye laser to the wavelength corresponding to the absorption state of the constituent.

19. The method of claim 13 wherein the second laser beam is tuned by an optical parametric oscillator laser to the wavelength corresponding to the absorption state of the constituent.

20. The method of claim 13 wherein the first, second and third laser beams are generated by a Nd:YAG laser.

21. The method of claim 13 wherein the decay emission of the absorption state is measured by an intensified charge-coupled device array.

22. The method of claim 13 wherein the second laser beam is oriented substantially normal to the first laser beam.

23. The method of claim 14 wherein the metal is selected from the group consisting of copper, iron, nickel, titanium and aluminum.

24. An ambient method for rapidly analyzing the amount of a constituent present in a sample wherein the sample is a fluid, the method comprising:

exposing a sample to a first laser beam, the beam having a suitable wavelength and intensity form a plasma of the micro-specimen, the plasma having a composition substantially the same as the composition of the sample;

exposing the plasma to a second laser beam, the second laser beam having a wavelength corresponding to an absorption state of a trace constituent to thereby excite fluoresce the absorption state and intensify the decay emission of the absorption state;

exposing the plasma to a third laser beam, the third laser beam having a wavelength longer than the wavelength of the second laser beam;

obtaining a net constituent intensity value by measuring the intensity of the decay emission of the absorption state from the plasma exposed to the second laser beam and subtracting the intensity of the decay emission of the absorption state from the plasma exposed to the third laser beam; and comparing the net constituent intensity value to a calibrated emission spectrum intensity value for the constituent.

25. An ambient method for rapidly detecting the presence of a trace element in a copper cathode, the method comprising:

exposing a sample of a cathode to a first laser beam, the beam having a suitable wavelength and intensity to ablate a micro-specimen from the sample surface and to form a plasma of the ablated micro-specimen, the plasma having a composition substantially the same as the composition of the sample;

exposing the plasma to a second laser beam, the second laser beam having a wavelength corresponding to an absorption state of a trace element to thereby excite fluoresce the absorption state and intensify the decay emission of the state;

obtaining a decay emission value for the absorption state that is greater than the background emission value; and comparing the decay emission value to a calibrated emission value for the element.

26. An apparatus for rapidly analyzing the amount of a constituent present in a sample under ambient conditions, the apparatus comprising:

means for generating a first laser beam, the first laser beam having a suitable wavelength and intensity to ablate a micro-specimen from the sample surface and to form a plasma of the micro-specimen, the plasma having a composition substantially the same as the composition of the sample;

means for generating a second laser beam, the second laser beam having a wavelength corresponding to an absorption state of the constituent to thereby excite fluoresce the absorption state and intensify the decay emission of the state;

means for measuring the intensity of the decay emission of the constituent absorption state to obtain the constituent intensity; and means for comparing constituent intensity value to a calibrated emission spectrum intensity value for the constituent.

27. The apparatus of claim 26 further comprising means for sequencing the delivery of the first and second laser beams to a sample.

28. The apparatus of claim 26 wherein the first laser beam and the second laser beam are generated by the same laser.

29. A portable apparatus for rapidly analyzing the amount of a constituent present in a sample under ambient conditions, the apparatus comprising:

means for generating a first laser beam, the first laser beam having a suitable wavelength and intensity to ablate a micro-specimen from the sample surface and to form a plasma of the micro-specimen, the plasma having a composition substantially the same as the composition of the sample;

means for generating a second laser beam, the second laser beam having a wavelength corresponding to an absorption state of the constituent to thereby excite fluoresce the absorption state and intensify the decay emission of the state;

means for measuring the intensity of the decay emission of the constituent absorption state to obtain the constituent intensity; and means for comparing constituent intensity value to a calibrated emission spectrum intensity value for the constituent.

30. An apparatus for rapidly analyzing the amount of a constituent present in a sample under ambient conditions, the apparatus comprising:

means for generating a first laser beam, the first laser beam having a suitable wavelength and intensity to ablate a micro-specimen from the sample surface and to form a plasma of the micro-specimen, the plasma having a composition substantially the same as the composition of the sample;

means for generating a second laser beam;

means for tuning the second laser beam to change the beam wavelength to correspond to the wavelength of an absorption state of the constituent to thereby excite fluoresce the absorption state and intensify the decay emission of the state;

means for measuring the intensity of the decay emission of the constituent absorption state to obtain the constituent intensity; and means for comparing constituent emission intensity value to a calibrated emission spectrum intensity value for the constituent.

31. An apparatus for rapidly analyzing the amount of a constituent present in a sample under ambient conditions, the apparatus comprising:

a first laser, the first laser producing a beam having a suitable wavelength and intensity to ablate a micro-specimen from the sample surface and to form a plasma of the micro-specimen, the plasma having a composition substantially the same as the composition of the sample;

a second laser, the second laser producing a second beam that has a first wavelength;

an optical parametric oscillator laser, which optical parametric oscillator laser changes the first wavelength of the second beam to a second wavelength that corresponds to an absorption state of the constituent to thereby excite fluoresce the absorption state and intensify the decay emission of the state;

a detector for measuring the intensity of the decay emission of the constituent absorption state to obtain the constituent intensity; and a computer to compare constituent emission intensity value to a calibrated emission spectrum intensity value for the constituent.

32. The apparatus of claim 31 further comprising a sequencer, the sequencer sequencing the firing of the first and second lasers.

33. The apparatus of claim 31 further comprising a probe, the probe comprising means to deliver the first and second beams to a sample and means to carry the emission decay signal to the detector.

34. The apparatus of claim 31 wherein the first and second lasers are Nd:YAG lasers.

35. An apparatus for rapidly analyzing the amount of a constituent present in a sample under ambient conditions, the apparatus comprising:

a first laser, the first laser producing a beam having a suitable wavelength and intensity to ablate a micro-specimen from the sample surface and to form a plasma of the micro-specimen, the plasma having a composition substantially the same as the composition of the sample;

a second laser, the second laser producing a second beam that has a first wavelength;

a tunable laser dye, which tunable laser dye changes the first wavelength of the second beam to a second wavelength that corresponds to an absorption state of the constituent to thereby excite fluoresce the absorption state and intensify the decay emission of the state;

a detector for measuring the intensity of the decay emission of the constituent absorption state to obtain the constituent intensity; and a computer to compare constituent emission intensity value to a calibrated emission intensity value for the constituent.

36. The apparatus of claim 35 further comprising a sequencer, the sequencer sequencing the firing of the first and second lasers.

37. The apparatus of claim 35 further comprising a probe, the probe comprising means to deliver the first and second beams to a sample and means to carry the emission decay signal to the detector.

* * * * *